(12) United States Patent
Pechstein et al.

(10) Patent No.: US 7,615,140 B2
(45) Date of Patent: Nov. 10, 2009

(54) POTENTIOMETRIC SENSOR WITH STATUS MONITORING

(75) Inventors: Torsten Pechstein, Radebeul (DE); Lars Kirsten, Mittweida (DE)

(73) Assignee: Endress + Hauser Conducta Gesellschaft fur Mess- und Regeltechnik mbH + Co. KG, Gerlingen (DE)

( * ) Notice: Subject to any disclaimer, the term of this patent is extended or adjusted under 35 U.S.C. 154(b) by 442 days.

(21) Appl. No.: 11/643,834

(22) Filed: Dec. 22, 2006

(65) Prior Publication Data

US 2007/0163881 A1  Jul. 19, 2007

(30) Foreign Application Priority Data

Dec. 23, 2005  (DE)  ........................ 10 2005 062 387

(51) Int. Cl.
*G01N 27/26* (2006.01)
(52) U.S. Cl. .................... 204/416; 204/406; 204/433
(58) Field of Classification Search ................. 204/416, 204/406, 433
See application file for complete search history.

(56) References Cited

U.S. PATENT DOCUMENTS

| 4,444,644 | A | * | 4/1984 | Hiramoto et al. | ............ | 204/406 |
| 5,583,462 | A | * | 12/1996 | Grasshoff | .................... | 327/262 |
| 6,624,637 | B1 | * | 9/2003 | Pechstein | .................... | 324/438 |
| 2004/0223287 | A1 | * | 11/2004 | Chung et al. | ................. | 361/235 |
| 2005/0230245 | A1 | * | 10/2005 | Morgenshtein et al. | ..... | 204/416 |
| 2006/0046375 | A1 | * | 3/2006 | Chou et al. | ................. | 438/216 |
| 2007/0089988 | A1 | * | 4/2007 | Chung et al. | ................. | 204/406 |

* cited by examiner

*Primary Examiner*—Bruce F Bell
(74) *Attorney, Agent, or Firm*—Bacon & Thomas, PLLC

(57) ABSTRACT

A potentiometric sensor for measuring a potentiometric variable of a medium comprises an ISFET whose gate region exhibits an ion-sensitive surface which can be exposed to the medium and which outputs an output signal that depends on the concentration of the ions at the ion-sensitive surface of the gate region. An evaluation circuit with a measuring input to which the output signal of the ISFET is applied is included, whereby the evaluation circuit is designed to output a measured value for the potentiometric variable, depending on the output signal. Also included is a measuring resistor which is arranged between the output of the ISFET and the input of the evaluation circuit, a monitoring circuit to determine the voltage drop over the measuring resistor, and a bridge section that is parallel to the measuring resistor to bridge the measuring resistor whereby the bridge section exhibits a switch with which the bridge section can be opened or closed.

5 Claims, 1 Drawing Sheet

POTENTIOMETRIC SENSOR WITH STATUS MONITORING

FIELD OF THE INVENTION

This invention refers to a potentiometric sensor with status monitoring whereby the sensor exhibits an ion-sensitive field effect transistor (ISFET) in particular.

BACKGROUND OF THE INVENTION

Potentiometric sensors with ISFETs are used to determine electrochemical potentials, particularly as pH sensors. Such sensors are discussed in the article by P. Bergveld ("Thirty Years of ISFETOLOGY" in Sensors and Actuators B 88, 2003, P. 1-20), for example.

For an ISFET to work, it is essential that there is no leak current which can impact the measurement of the electrochemical potential. If a significant leak current is present, this implies that the potentiometric sensor is defective. For this reason, it is vital to monitor the sensor for leak current.

Common current monitoring systems with a shunt resistor in the measuring section cannot be considered, however, as currents in the range of 1 nA have to be detected which would either require a large resistance, which cannot be reconciled with the measurement, or a complex evaluation circuit which would be too expensive for the sensors in question.

In addition, a leak current can be detected using the counter-current principle. Here, a controlled current source is integrated in the circuit to be monitored which should impress a current that counteracts the leak current. An additional measuring device, which can determine whether the sum of the leak current and the counter current results in a value "zero", controls the current source. The system can then determine to what extent a leak current is present on the basis of the control signal required. The counter-current principle is also not suitable for monitoring a potentiometric sensor because it involves increased power consumption, which—particularly for sensors with galvanically isolated, inductively coupled interfaces, as sold by the patent applicant under the name Memosens—is not readily available for potentiometric sensors. Similarly, a counter-current system involves increased costs which are not justifiable for potentiometric sensors.

SUMMARY OF THE INVENTION

An object of this invention is thus to provide viable leak current monitoring for a potentiometric sensor with an ISFET.

This object is achieved by a potentiometric sensor for measuring a potentiometric variable of a medium which comprises: a ISFET whose gate region exhibits an ion-sensitive surface which can be exposed to the medium and which outputs an output signal which depends on the concentration of the ions at the ion-sensitive surface of the gate region; a evaluation circuit with a measuring input to which the output signal of the ISFET is applied, whereby the evaluation circuit is designed to output a measured value for the potentiometric variable depending on the output signal; a measuring resistor that is arranged between the output of the ISFET and the input of the evaluation circuit; a monitoring circuit to determine the voltage drop over the measuring resistor; and a bridge section running parallel to the measuring resistor to bridge the measuring resistor whereby the bridge section exhibits a switch with which the bridge section can be opened and closed.

The potentiometric sensor can be a pH sensor in particular.

BRIEF DESCRIPTION OF THE DRAWING

The invention will now be explained using a sample version illustrated in the drawing.

DETAILED DESCRIPTION

Figure 1:
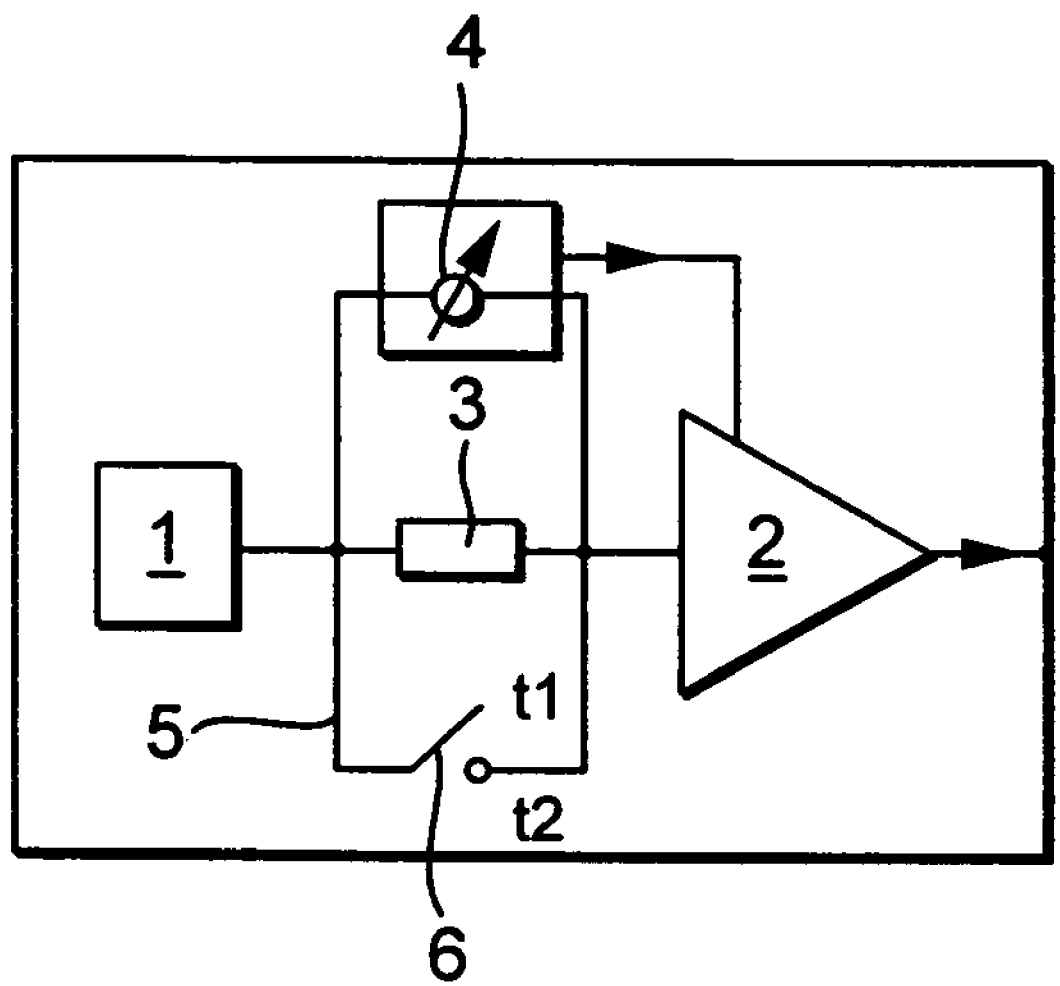
FIG. 1 shows a block circuit diagram of a potentiometric sensor as per the invention.

In this version, the potentiometric sensor is a pH sensor. It comprises a pH-sensitive ISFET (1) whose output is connected to the input of an evaluation circuit (2) in a measuring section and this evaluation circuit (2) outputs a pH value depending on the output signal of the ISFET (1).

A 100 Megaohm measuring resistor (3) is arranged in the measuring section, whereby a monitoring circuit (4) determines the voltage drop over the measuring resistor (3). In a simple version of the invention, a comparator is provided which compares the voltage drop determined against a configurable limit value, and triggers an alarm if the limit value is exceeded.

As the measuring resistor (3) can distort the output signal of the ISFET, a bridge section (5) is provided parallel to the measuring resistor (3) and bridges the measuring resistor (3). The bridge section (5) comprises a clocked switch (6) which is opened at times t1 and closed at times t2. The duty factor t2:t1 is 32:1, for example. The pH can be measured when the switch is closed and the leak current is monitored when the switch is open.

The switch can be clocked whereby the output signal for determining the potentiometric measured variable is evaluated when the switch is closed and the measuring resistor is monitored when the switch is open.

The measuring resistor can be designed such that a voltage drop between 1 mV and 100 mV takes place at a current of 1 nA, i.e. the measuring resistor can exhibit a value from between 1 Megaohm and 100 Megaohm.

The duty factor of the switch is not critical. The switch can be closed most of the time so that the potentiometric variable can be determined and the switch only has to be opened a short part of the time for leak current monitoring. A duty factor greater than 10:1 or even greater than 100:1 is possible.

The switch and/or the monitoring circuit can be arranged separate from the evaluation circuit or be implemented with the circuit in an assembly.

In another embodiment of the invention, the potentiometric sensor as per the invention comprises a monitoring output which, depending on the leak current value determined or the pattern of the leak current value over time, outputs an alarm if a leak current value is exceeded or if leak current overshoot is imminent, or gives a prognosis on the remaining service life.

The invention claimed is:

1. A potentiometric sensor for measuring a potentiometric variable of a medium, comprising:

a ISFET whose gate region has an ion-sensitive surface which can be exposed to the medium and which outputs an output signal which depends on the concentration of the ions at the ion-sensitive surface of the gate region;

an evaluation circuit with a measuring input to which the output signal of said ISFET is applied, wherein said evaluation circuit is designed to output a measured value for the potentiometric variable depending on the output signal;

a measuring resistor that is arranged between the output of said ISFET and the input of said evaluation circuit;

a monitoring circuit to determine the voltage drop over said measuring resistor; and a bridge section running parallel to said measuring resistor to bridge said measuring resistor wherein said bridge section exhibits a switch with which said bridge section can be opened and closed.

2. The potentiometric sensor as defined in claim 1, wherein:

said switch is clocked and the output signal for determining the potentiometric measured variable is evaluated when said switch is closed and said measuring resistor is monitored when said switch is open.

3. The potentiometric sensor defined in claim 1, wherein:

said monitoring exhibits a monitoring output that outputs an alarm depending on the leak current determined or the pattern of the leak current value over time.

4. The potentiometric sensor as defined in claim 1, wherein:

said monitoring circuit exhibits a monitoring output which, depending on the leak current determined or the pattern of the leak current value over time, outputs a prognosis on the remaining service life of the sensor.

5. The potentiometric sensor as defined in claim 1, wherein:

the potentiometric sensor is a pH sensor.

* * * * *